United States Patent [19]

Peery et al.

[11] 4,318,400
[45] Mar. 9, 1982

[54] MEDICAL INFUSOR

[75] Inventors: John R. Peery; Peter F. Carpenter, both of Palo Alto; William K. Griesinger, Saratoga, all of Calif.

[73] Assignee: Alza Corporation, Palo Alto, Calif.

[21] Appl. No.: 113,224

[22] Filed: Jan. 18, 1980

[51] Int. Cl.³ .............................................. A61M 5/00
[52] U.S. Cl. .......................... 128/214 F; 128/DIG. 12
[58] Field of Search ............ 128/214 R, 214 E, 214 F, 128/213, 215, 216, DIG. 12, DIG. 13; 222/95, 105, 106, 206, 212, 23, 386.5

[56] References Cited

U.S. PATENT DOCUMENTS

| | | | |
|---|---|---|---|
| 3,412,906 | 11/1968 | Dinger | 128/DIG. 12 |
| 3,486,539 | 12/1969 | Jacuzzi | 128/DIG. 12 |
| 3,507,278 | 4/1970 | Werding | 128/214 F |
| 3,895,631 | 7/1975 | Buckles et al. | 128/213 |
| 4,140,117 | 2/1979 | Buckles et al. | 128/213 |
| 4,201,207 | 5/1980 | Buckles et al. | 128/214 F |

Primary Examiner—Stephen C. Pellegrino
Attorney, Agent, or Firm—Steven F. Stone; Edward L. Mandell; Paul L. Sabatine

[57] ABSTRACT

A portable elastomeric bladder-powered infusor for dispensing drug in liquid form under pressure at a predetermined flow rate is disclosed. The main elements of the infusor are a tubular housing, a plug/flow control assembly fixed in one end of the bladder, an axially slidable piston/filling port assembly within the housing, and a tubular bladder. The plug and piston assemblies each has an axial post about which the bladder ends are attached. When the bladder is not charged with drug, the posts fill the bladder's lumen and their ends abut. Drug is charged to the infusor by inserting a drug-filled syringe into the open end of the housing with the syringe's needle entering an axial bore in the piston, penetrating a septum that blocks the bore, and extending into the axial post. The force exerted on the piston by the syringe is transmitted to the fixed plug assembly via the axial posts. Drug is plunged from the syringe causing the posts to separate and the bladder to expand axially and radially. Once the bladder is filled, the syringe is withdrawn, with the septum sealing itself. The drug is dispensed from the bladder via the plug/flow control assembly and a conduit that is connected to that assembly and extends to the infusion site.

6 Claims, 5 Drawing Figures

MEDICAL INFUSOR

TECHNICAL FIELD

The invention relates to an infusor for dispensing drugs in liquid form to a patient.

DISCLOSURE OF PRIOR ART

The infusor of this invention was developed as an improvement of the infusor disclosed in commonly owned U.S. Pat. Nos. 3,895,631 and 4,140,117. The infusor of those patents involves two basic components: a replaceable cartridge assembly that is designed to hold the drug within an elastomer bladder; and a housing into which the cartridge is inserted. The housing is shaped to fit on an extremity of the patient and it contains an adjustable flow control subassembly. These patented infusors performed satisfactorily. But, they are complex in that they are composed of a great many parts. Accordingly, they cannot be easily manufactured in an automated manner and are thus costly relative to the conventional gravity-feed infusion apparatus used in health care.

DISCLOSURE OF THE INVENTION

An object of the present invention is to provide a compact, lightweight infusor that is less complicated and easier to manufacture than the above described patented infusors, and is capable of being filled with a standard syringe.

The invention is an infusor for dispensing a liquid under pressure at a predetermined flow rate. It has the following components: a tubular housing; a plug fixed in one end of the housing and having an aperture that extends through the plug; a piston within the housing that is adapted to slide axially within the housing; a tubular elastomeric bladder for receiving the liquid under pressure, the ends of which are sealingly attached to the plug and piston, respectively, with the lumen of the bladder communicating with the aperture in the plug; solid lumen filling means within the lumen of the bladder which substantially fills the lumen of the bladder when the bladder is deflated; a conduit connected to the aperture in the plug, the conduit and aperture together defining a dispensing passageway for transporting the liquid from the bladder to the infusion site; and a flow regulator in the dispensing passageway for permitting the liquid to flow from the bladder through the dispensing passageway at said predetermined rate.

A preferred embodiment of the infusor comprises in combination a cylindrical housing; a plug fixed in one end of the housing and having an axial aperture; a first axial post extending from the interior side of said plug and having an axial aperture that communicates with the axial aperture in the plug, the axial apertures in the plug and first axial post defining a dispensing passageway; a piston within the housing that has an axial aperture and is adapted to slide axially within the housing; a second axial post extending from the interior side of the piston toward the first axial post and having an axial aperture, the axial apertures in the piston and second axial post defining a filling passageway adapted to receive a filling needle; a septum within the filling passageway that seals the passageway and is adapted to be punctured by the filling needle and self-seal when the filling needle is withdrawn therefrom; a tubular elastomeric bladder for receiving the liquid and holding the liquid under pressure, the ends of which are sealingly attached about the first and second axial posts, respectively, such that when the bladder is deflated the first and second axial posts substantially fill the lumen of the bladder and the free ends of the first and second axial posts abut each other thus resisting pushing force generated during septum puncture by the filling needle; a flow regulator in the dispensing passageway for permitting the liquid to flow from the bladder through the dispensing passageway at said predetermined flow rate; and a conduit connected to said dispensing passageway for transporting the liquid from the dispensing passageway to the infusion site.

DESCRIPTION OF INFUSORS SHOWN IN DRAWINGS

Figure 1:
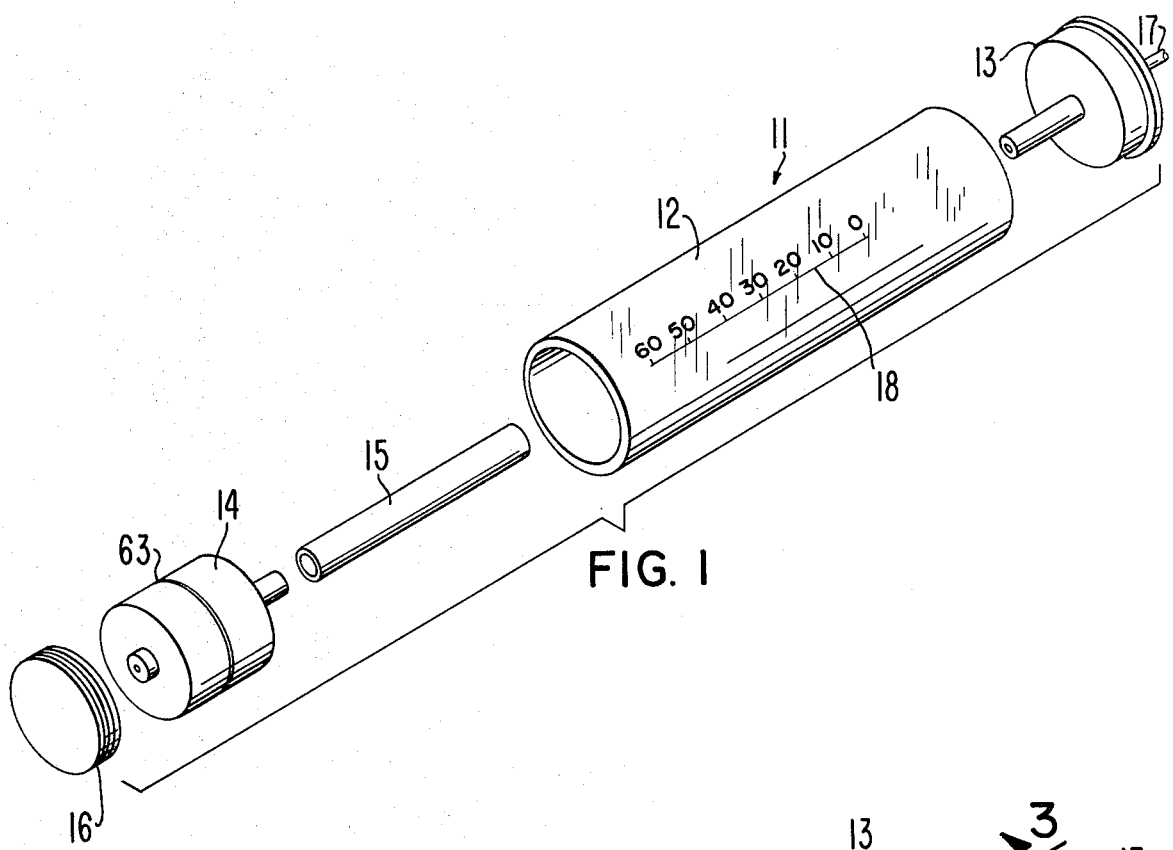
FIG. 1 is an exploded, perspective view of the preferred embodiment of the infusor.
Figure 2:
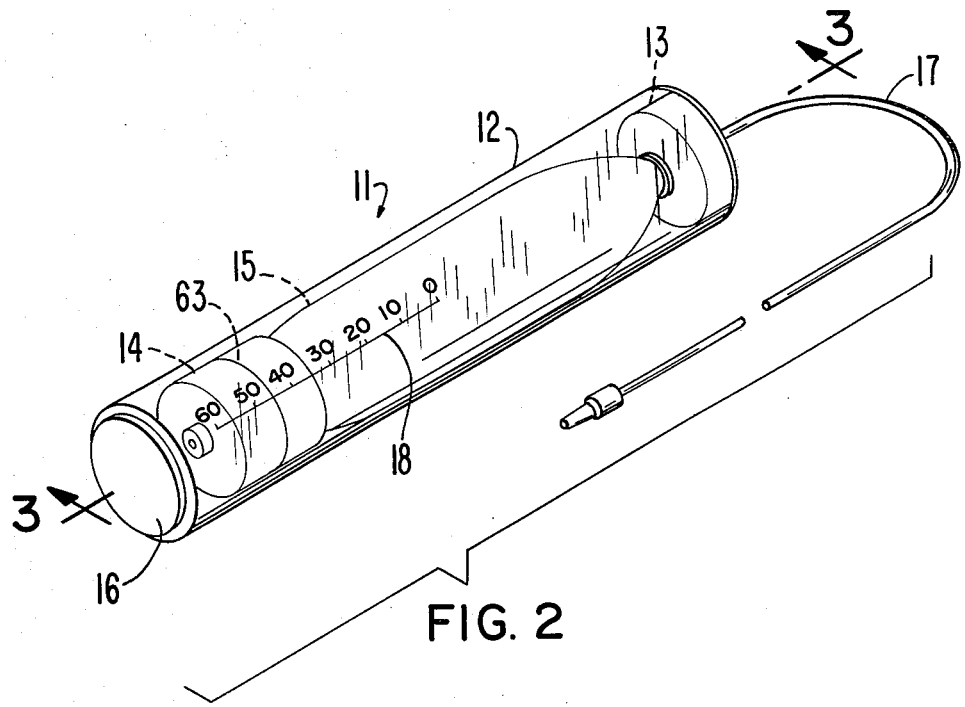
FIG. 2 is a perspective view of the infusor of FIG. 1 with the bladder of the infusor filled with liquid.

FIGS. 1 and 2 depict the basic elements of the preferred embodiment of the infusor, which is generally designated 11 in the drawings. Those elements are: a tubular housing 12; a plug/flow control assembly 13; a piston/filling port assembly 14; an elastomeric bladder 15; a filling port cover 16; and a delivery conduit 17. Infusor 11 is symmetrical about the axis of housing 12. Its manufacture is thus simplified since no radial orientation of parts is required during its assembly.

Except for the delivery conduit 17, the elements of the infusor are contained within the lumen of cylindrical housing 12. Housing 12 may be made from various thermoplastic polymers. A graduated volume scale 18 is imprinted, scribed, or otherwise applied to the housing wall. As described below this volume scale indicates the quantity of liquid contained within bladder 15. It is graduated in milliliters from 1 to 60 ml, the capacity of bladder 15 being 60 ml.

Figure 3:
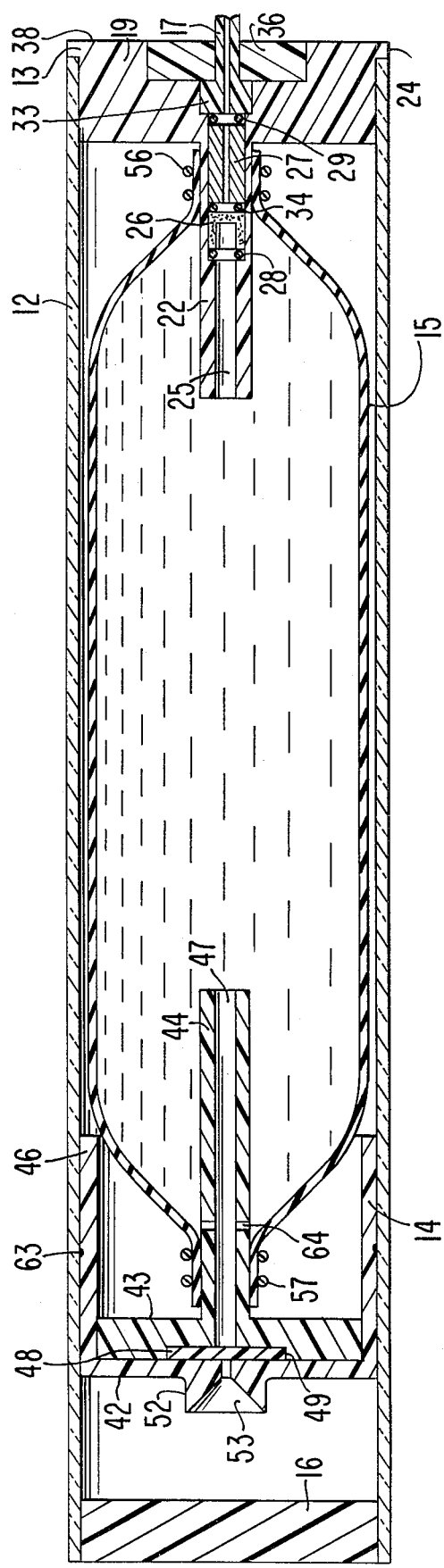
FIG. 3 is an enlarged, sectional view of the infusor of FIG. 1 taken along line 3—3 of FIG. 2.
Figure 4:
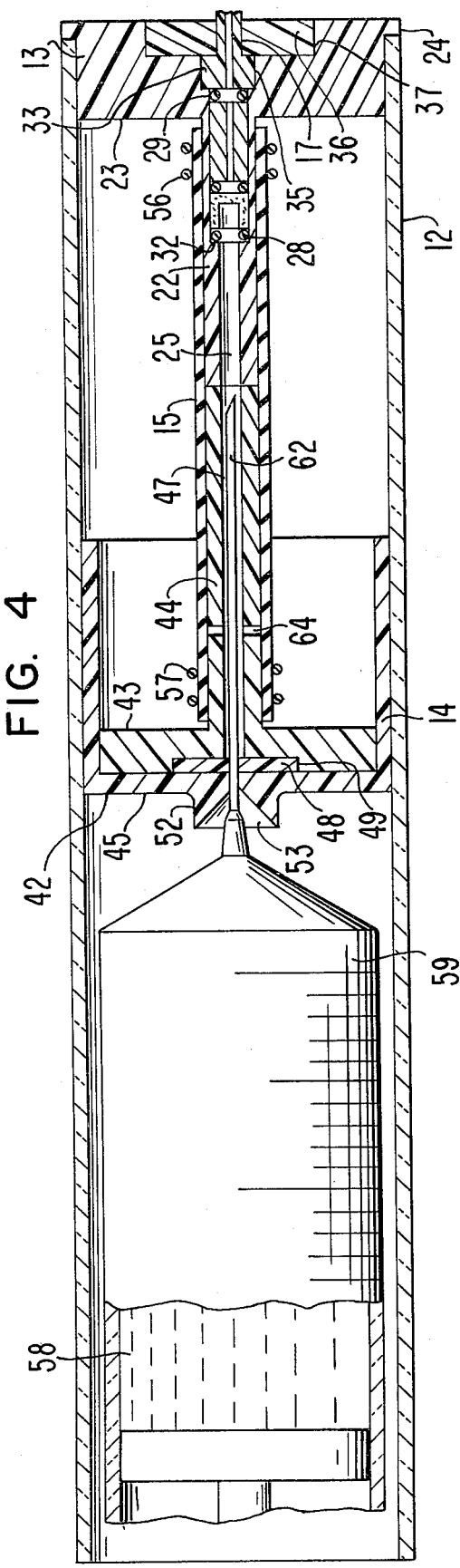
FIG. 4 is an enlarged sectional view of the infusor of FIG. 1 showing the infusor bladder ready to be filled with liquid from a syringe.

As shown in FIGS. 3 and 4, plug/flow control assembly 13 is fixed in one end of housing 12. The fixation may be effected by adhesion, fusion, or other appropriate means. Assembly 13 includes a main body 19 and an axial post 22 that is integrally connected to the inner side 23 of body 19. The body has a peripheral shoulder 24 against which the end of housing 12 is seated. An axial bore 25 of varying diameter extends through body 19 and post 22. Bore 25 serves as an outlet port for transmitting liquid from bladder 15 to delivery conduit 17. Within bore 25 are a cup-shaped particle filter 26 and a capillary flow control element 27. Filter 26 and element 27 are compression sealed within bore 25 through the use of O-rings 28 and 29. O-ring 28 is seated between a shoulder 32 at a diameter transition in bore 25 and the inner end of filter 26. O-ring 29 is seated between the outer end of element 27 and the enlarged diameter inner end 33 of delivery conduit 17. A third O-ring 34 forms a seal about the perimeter of the interface between filter 26 and capillary element 27. End 33 of conduit 17 is fusion sealed in an enlarged diameter segment 35 of bore 25. End 33 (and in turn element 27 and filter 26) is held under compression by a disc-shaped plug 36 that is fixed by adhesion, fusion, or other fixation means within a recess 37 in the outer side 38 of body 19. Plug 36 has an axial opening through which delivery conduit 17 extends.

Piston/filling port assembly 14 is slidably housed within the lumen of housing 12. It includes a head 42, a base 43 and an axial post 44 extending from the inner side of base 43 toward the axial post 22 of plug/flow control assembly 13. Head 42 has an end wall 45 that traverses the lumen of housing 12 and a cylindrical side wall 46 that extends laterally along the inside of housing 12. An axial bore 47 extends through end wall 45, base 43, and axial post 44. Base 43 is affixed to head 42 by adhesion, fusion, or other affixation means. A septum 48 is contained within a recess 49 in the outer side of base 43. Septum 48 is sealingly compressed at its perimeter. it traverses and closes bore 47. It is made from a material, such as an elastomer, that is capable of being punctured and resealing itself after the puncturing instrument is withdrawn. The outer side of end wall 45 has an axial projection 52 with a conical recess 53 that opens into axial bore 47. As described in detail below recess 53 acts as a guide for the instrument that is used to charge bladder 15 with liquid.

As shown in FIG. 4, when bladder 15 is deflated (not filled) it fits about axial posts 22 and 44 in sleeve-like fashion. The outer diameters of posts 22 and 44 are not greater than the inner diameter of bladder 15 when it is deflated. Preferably the outer diameters of the posts are slightly smaller than the inner diameter of the deflated bladder. A pair of spring clamps 56 and 57 around the ends of the bladder effect fluid tight joinder between the posts and the bladder ends. The axial posts 22 and 44 substantially fill the lumen of bladder 15 and their free ends abut each other when the bladder is deflated. As discussed below, these features contribute to the complete discharge of liquid from the bladder and the ease with which the bladder may be charged with liquid.

FIG. 4 shows the infusor ready to be charged, with a drug in liquid form, designated 58. As shown, a syringe 59 containing liquid 58 has been inserted into the lumen of housing 12 with the needle 62 of the syringe puncturing septum 48 and extending into the axial bore 47 of assembly 14. In this insertion procedure recess 53 guides the end of needle 62 into the opening of bore 47 and the force applied to assembly 14 to puncture septum 48 is transmitted to fixed plug/flow control assembly 13 via the abutting posts 22, 44. Piston/filling port assembly 14 is thus supported during this initial step in the filling operation. Further, post 44 guides needle 62 after the septum is punctured and shields the bladder from being punctured.

Once the syringe has been positioned as shown in FIG. 4, the plunger (not shown) of the syringe is depressed to eject liquid 58 into bladder 15 via needle 62, and bore 47. It should be noted that there is no seal between the free ends of posts 22, 44 so that the liquid is free to flow from bore 47 into the bladder. It should also be noted that the conduit 17 must be capped, valved or otherwise closed off at this point in time to prevent the premature dispensing of the liquid from the infusor. As liquid is ejected from the syringe into the bladder, the bladder expands axially and radially until it assumes the expanded (filled) state depicted in FIG. 3. The volume of liquid in the bladder may be determined by observing the location of an indicator line 63 in wall 46 relative to volume scale 18. Housing 12 is transparent in the area of scale 18 so that indicator line 63 may be so observed. Piston assembly 14 slides axially within the housing to accommodate the axial expansion of the bladder. As it does so, line 63 moves along scale 18. When the bladder is fully filled, line 63 will register with the 60 ml mark on scale 18. When filled the bladder wall is spaced from posts 22, 44 except at the clamped ends and a radial air vent 64 traversing post 44 is exposed and unobstructed. The bladder wall is also preferably spaced from housing 12, except that gravity may cause a portion of the bladder wall to touch the housing. Such spacing prevents the housing from constricting the bladder.

Once bladder 15 is filled with liquid 58 the infusor is tipped into a vertical position with the piston-filling port uppermost. This causes any air that may have been trapped in the bladder to rise to the piston-filling port end of the bladder. The syringe is then withdrawn partly so that the tip of the needle resides in the segment of bore 47 between septum 48 and air vent 64 and any air trapped in the bladder is sucked therefrom into the syringe via air vent 64. The syringe is then withdrawn completely from the infusor, with septum 48 sealing itself and closing bore 47 to liquid flow. Filling port cover 16 is then inserted flush into the open end of housing 12 to prevent patients from tampering with the contents of the housing. Infusor 11 is then ready for use.

For use on ambulatory patients, infusor 11 will normally be attached directly to an extremity with a strap accessory or to the body or clothing with an appropriate holster, pouch, belt, or similar attachment means. A cannula is then inserted at the infusion site. The end of delivery conduit 17 is then attached to the cannula. Liquid 58 will then commence to be infused into the patient from the bladder through bore 25, filter 26, the capillary of element 27, conduit 17 and the cannula. The flow rate of liquid to the patient will depend upon the dimension of the capillary of element 27, the pressure exerted on the liquid by the bladder, and the viscosity of the liquid. At a fixed capillary dimension and pressure, flow rate may be correlated solely to viscosity and thus may be predetermined accurately.

When infusor 11 is exhausted, bladder 15 will appear as in FIG. 4. The infusor is capable of dispensing essentially all of its liquid charge because posts 22, 44 occupy the deflated volume of the lumen of bladder 15 leaving no room for residual liquid.

Figure 5:
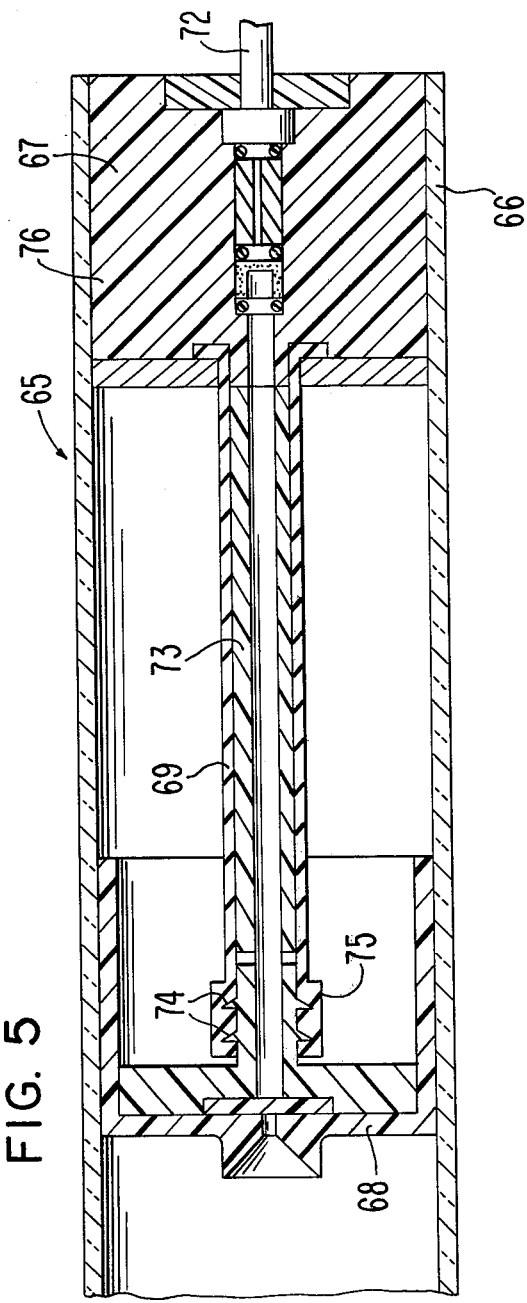
FIG. 5 is an enlarged sectional view similar to FIG. 4 of another embodiment of the infusor.

FIG. 5 illustrates an alternate, less preferred infusor, generally designated 65. It is similar to infusor 11 except as regards the attachment of the bladder ends, the bladder lumen filling means, and the location of the liquid flow control regulator. Since infusor 65 is similar to infusor 11 in other respects, only the above mentioned differences are described in detail hereinafter.

The basic elements of infusor 65 are: a tubular housing 66; a plug/flow control assembly 67; a piston/filling port assembly 68; an elastomeric bladder 69; a filling port cover (not shown); and a delivery conduit 72. Piston/filling port assembly 68 includes an integral axial post 73 that extends nearly the entire length of deflated bladder 69 and abuts against the inner side of assembly 67 when bladder 69 is deflated. Post 73 is an alternate bladder lumen filling means to posts 22, 44 of infusor 11. Bladder 69 fits about post 73 in sleeve-like fashion. Barbs 74 on the piston end of post 73 anchor enlarged diameter end 75 of the bladder to the post. The other end of the bladder is sealingly seated within assembly 67. Post 73, as posts 22 and 44 of infusor 11, functions as a filling needle guide and provides support for assembly 68 during the filling operation. A filter and flow control subassembly, generally designated 76, is contained wholly within the body of assembly 67 rather than partly within an axial post and partly within the main body of the assembly as in infusor 11.

Modifications of the embodiments shown in the drawings and described above that are obvious to those of skill in the medical device and/or mechanical arts are intended to be within the scope of the following claims. Such modifications include, without limitation, other bladder lumen filling means such as pair of axial posts similar to but shorter than posts 22, 44 with a "floating" post segment therebetween or a multiplicity of spherical bodies, other means for attaching the bladder ends to the plug and piston assemblies, other bladder filling means such as a radial inlet to a post aperture, and other flow regulators such as porous plugs, fiber bundles, porous films or known adjustable flow regulators.

We claim:

1. An infusor for dispensing a liquid under pressure at a predetermined flow rate comprising in combination:
   a. a tubular housing;
   b. a plug fixed in one end of the housing having an aperture extending therethrough;
   c. a piston within the housing that is adapted to slide axially within the housing;
   d. a tubular elastomeric bladder for receiving the liquid under pressure, the ends of which are sealingly attached to the plug and piston, respectively, with the lumen of the bladder communicating with the aperture in the plug;
   e. solid lumen filling means within the lumen of the bladder said means extending between the inner side of the piston and the inner side of the plug and substantially filling the lumen of the bladder when the bladder is deflated;
   f. a conduit connected to the aperture in the plug, the conduit and aperture together defining a dispensing passageway for transporting the liquid from the bladder to the infusion site; and
   g. a flow regulator in the dispensing passageway for permitting the liquid to flow from the bladder through the dispensing passageway at said predetermined rate.

2. The infusor of claim 1 wherein the solid lumen filling means is at least one axial post that extends between the inner side of the piston and the inner side of the plug whereby when the bladder is deflated and axial force is applied to the piston in the direction of the plug, said force is transmitted via the axial post to the plug.

3. The infusor of claim 1 wherein the solid lumen filling means comprises a multiplicity of free floating spherical bodies.

4. An infusor for dispensing a liquid under pressure at a predetermined flow rate comprising in combination:
   (a) a cylindrical housing;
   (b) a plug fixed in one end of the housing and having an axial aperture;
   (c) a first axial post extending from the interior side of said plug and having an axial aperture that communicates with the axial aperture in the plug, the axial apertures in the plug and first axial post defining a dispensing passageway;
   (d) a piston within the housing that has an axial aperture and is adapted to slide axially within the housing;
   (e) a second axial post extending from the interior side of the piston toward the first axial post and having an axial aperture, the axial apertures in the piston and second axial post defining a filling passageway adapted to receive a filling needle;
   (f) a septum within the filling passageway that seals the passageway and is adapted to be punctured by the filling needle and self-seal when the filling needle is withdrawn therefrom;
   (g) a tubular elastomeric bladder for receiving the liquid and holding the liquid under pressure, the ends of which are sealingly attached about the first and second axial posts, respectively, such that when the bladder is deflated the first and second axial posts substantially fill the lumen of the bladder and the free ends of the first and second axial posts abut each other;
   (h) a flow regulator in the dispensing passageway for permitting the liquid to flow from the bladder through the dispensing passageway at said predetermined flow rate; and
   (i) a conduit connected to said dispensing passageway for transporting the liquid from the dispensing passageway to the infusion site.

5. The infusor of claim 4 wherein the second axial post has a radial aperture inwardly of the site of attachment of the bladder thereto, said radial aperture communicating with the axial aperture of the second axial post.

6. The infusor of claim 4 wherein the ends of the bladder are attached about the first and second axial posts by means of barbs on the exteriors of the first and second axial posts that penetrate the bladder wall.

* * * * *